US00PP23023P3

(12) United States Plant Patent
Perl et al.

(10) Patent No.: US PP23,023 P3
(45) Date of Patent: Sep. 11, 2012

(54) GRAPEVINE NAMED 'SWEET JASPER'

(50) Latin Name: ***Vitis vinifera* L.**
Varietal Denomination: SWEET JASPER

(75) Inventors: Avichai Perl, Rishon Lezion (IL); Nachman Sahar, Rehovot (IL); Oded Degani, Moshav Sde Moshe (IL); Tatiana Okun, Rehovot (IL); Arie Sarfian, Nes-Ziona (IL); Hanan Bazak, Carmei Yossef (IL); Refael Eliassi, Neve Yamin (IL); Ahuva Daos, Ganey Hmoshava Mazkeret Batia (IL)

(73) Assignee: State of Israel, Ministry of Agriculture & Rural Development, Agricultural Research Organization, Bet Dagan (IL)

( * ) Notice: Subject to any disclaimer, the term of this patent is extended or adjusted under 35 U.S.C. 154(b) by 0 days.

(21) Appl. No.: 12/929,133

(22) Filed: Jan. 3, 2011

(65) Prior Publication Data

US 2011/0277199 P1 Nov. 10, 2011

(30) Foreign Application Priority Data

Jan. 4, 2010 (IL) ..... PBR 4235

(51) Int. Cl.
*A01H 5/00* (2006.01)

(52) U.S. Cl. ..... Plt./207

(58) Field of Classification Search ..... Plt./207
See application file for complete search history.

*Primary Examiner* — Annette Para
(74) *Attorney, Agent, or Firm* — Foley & Lardner LLP

(57) ABSTRACT

This invention relates to a new and distinct variety of grapevine named 'SWEET JASPER'. The new early ripening, very fertile grapevine variety is particularly characterized by an attractive berry color, a very uniform bunch and a firm berry with tender crunchy skin.

5 Drawing Sheets

Botanical name of the genus and species of the plant claimed: *Vitis vinifera* L.

Variety denomination: 'SWEET JASPER'.

PRIORITY CLAIM

This application claims priority under 35 U.S.C. §119(f) of the Israeli Plant Breeders' Rights Application No. 4235 filed Jan. 4, 2010.

BACKGROUND OF THE INVENTION

The present invention relates to a new and distinct grapevine variety, botanically known as *Vitis vinifera* L., and hereinafter referred to by its variety denomination 'SWEET JASPER'.

The new grapevine 'SWEET JASPER' is a product of a controlled breeding program conducted by the inventors, Avichai Perl, Nachman Sahar, Oded Degani, Tatiana Okun, Arie Sarfian, Hanan Bazak, Refael Eliassi and Ahuva Daos at The Volcani Center, located in Bet Dagan, Israel. The objective of the breeding program was to develop a new early ripening, very fertile grapevine variety particularly characterized by attractive berries with yellowish green color which are uniform in size and shape and are firm with tender crunchy skin.

The new grapevine 'SWEET JASPER' originated from a cross made by the inventors in 2004 at The Volcani Center. The female or seed parent is the grapevine *Vitis vinifera* L indicated as 'ARO 2117' (unpatented), in the inventors' collection located in Bet Dagan, Israel, and the male or pollen parent is the grapevine *Vitis vinifera* L. indicated as 'ARO 1717' (unpatented), in the inventors' collection.

The new grapevine 'SWEET JASPER' was observed and selected by the inventors within the progeny of the stated cross in a controlled environment in 2007 at The Volcani Center.

Asexual propagation of the new grapevine variety by bud grafting was first performed in January 2008 at The Volcani Center, and has demonstrated that the combination of characteristics as herein disclosed for the new variety is firmly fixed and retained through successive generations of asexual propagation. The new cultivar propagates true-to-type.

SUMMARY OF THE INVENTION

'SWEET JASPER' can be grown in various climates and growing conditions. The variety produces and maintains a strong vigorous plant and consistent fruit production from end June through end July in Bet Dagan, Israel.

The following traits have been repeatedly observed and are determined to be characteristics of 'SWEET JASPER', which in combination distinguish this grapevine as a new, unique and distinct variety.

1. Very fertile;
2. Early ripening;
3. Firm berry with tender crunchy skin;
4. Attractive yellow green berry color; and
5. Berries which are uniform in size and shape.

Plants of the new grapevine 'SWEET JASPER' differ from plants of the parents *Vitis vinifera* L. 'ARO 2117' (unpatented) and *Vitis vinifera* L. 'ARO 1717' (unpatented), in the following characteristics described in Table 1.

TABLE 1

Comparison with parent varieties.

| Characteristic | New Variety 'SWEET JASPER' | Female Parent 'ARO 2117' (unpatented) | Male Parent 'ARO 1717' (unpatented) |
|---|---|---|---|
| Berry shape | cylindrical | rounded | elongated |
| Berry color of skin | yellowish green | yellow green | yellow green |
| Berry thickness of skin | thin | very thick | medium |
| Seeds | absent | absent | absent |

Of the many commercial varieties known to the present inventors, the most similar to the new grapevine 'SWEET JASPER' are *Vitis vinifera* L. 'SUGRAONE' (U.S. Plant Pat. No. 3,106) and *Vitis vinifera* L. 'PRIME' (registered for Israeli Plant Breeders' Rights No. 1467), which differ from the new grapevine 'SWEET JASPER' in the characteristics described in Table 2:

TABLE 2

Comparison with similar varieties.

| Characteristic | New Variety 'SWEET JASPER' | Comparison Variety 'SUGRAONE' (patented) | Comparison Variety 'PRIME' (registered) |
|---|---|---|---|
| Berry shape | cylindrical | obtuse ovate | oblong |
| Berry color of skin | yellowish green | yellow green | yellow green |
| Berry thickness of skin | thin | medium | medium |
| Seeds | absent | absent | absent |

BRIEF DESCRIPTION OF THE PHOTOGRAPHS

The accompanying photographs illustrate the overall appearance of the new grapevine 'SWEET JASPER' showing the colors as true as is reasonably possible with colored reproductions of this type. Colors in the photographs may differ slightly from the color values cited in the detailed morphological description, which accurately describe the color of 'SWEET JASPER'.

DETAILED MORPHOLOGICAL DESCRIPTION

Figure 1:
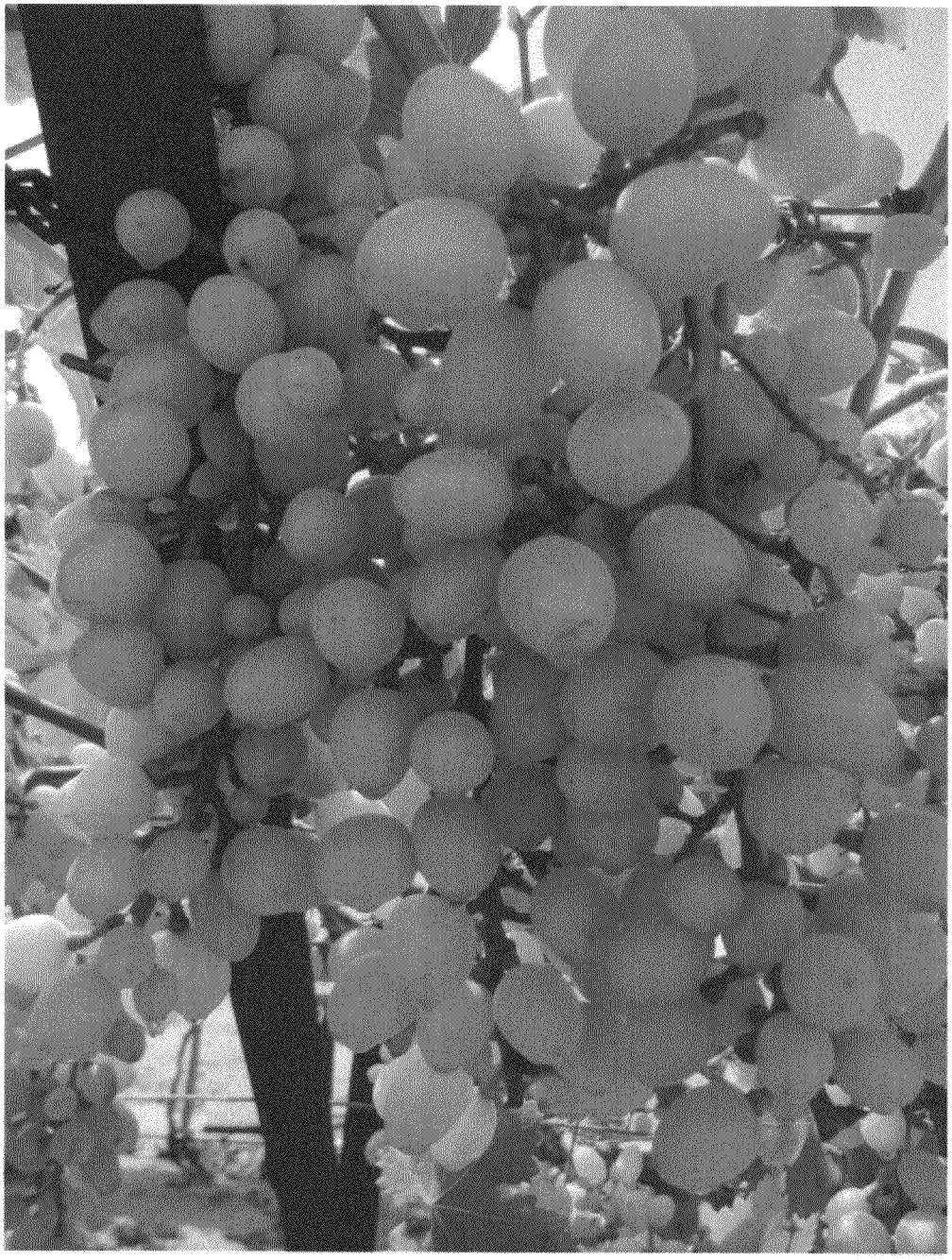
FIG. 1 shows a typical bunch of 'SWEET JASPER' on the plant.
Figure 2:
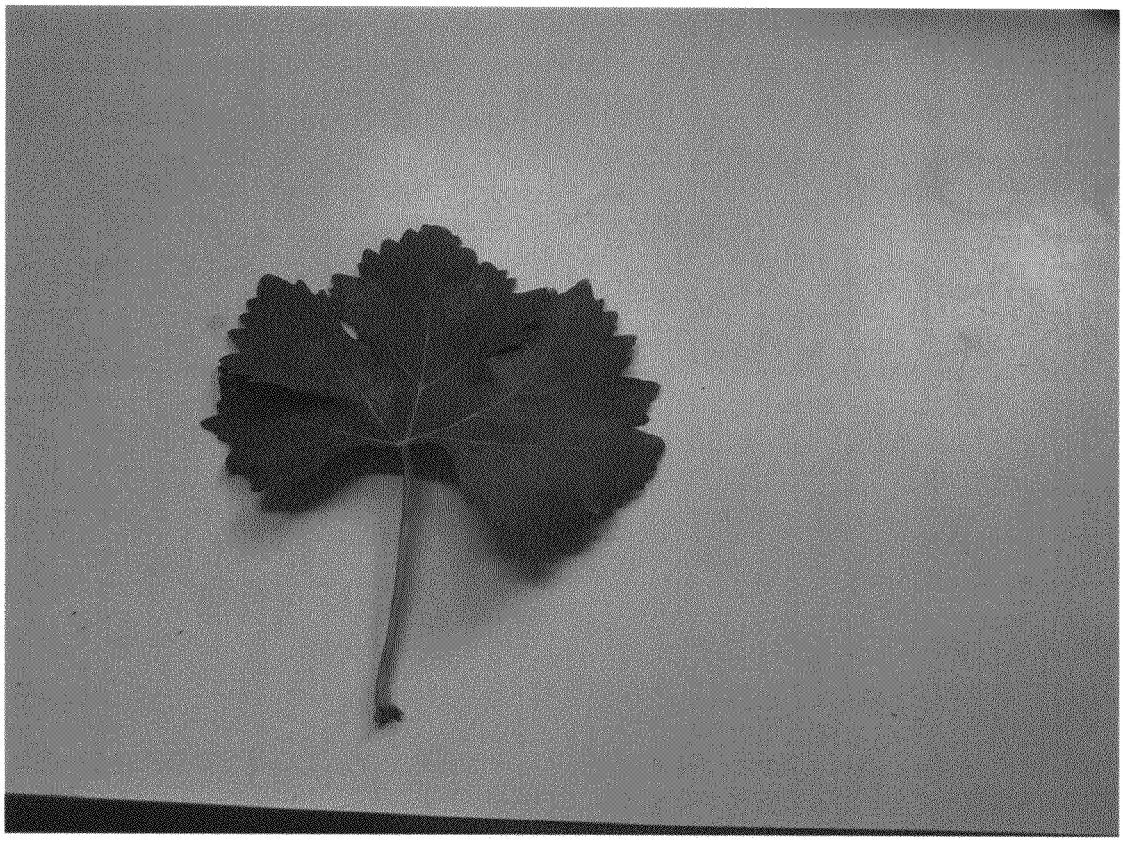
FIG. 2 shows a typical mature leaf of 'SWEET JASPER'.
Figure 3:
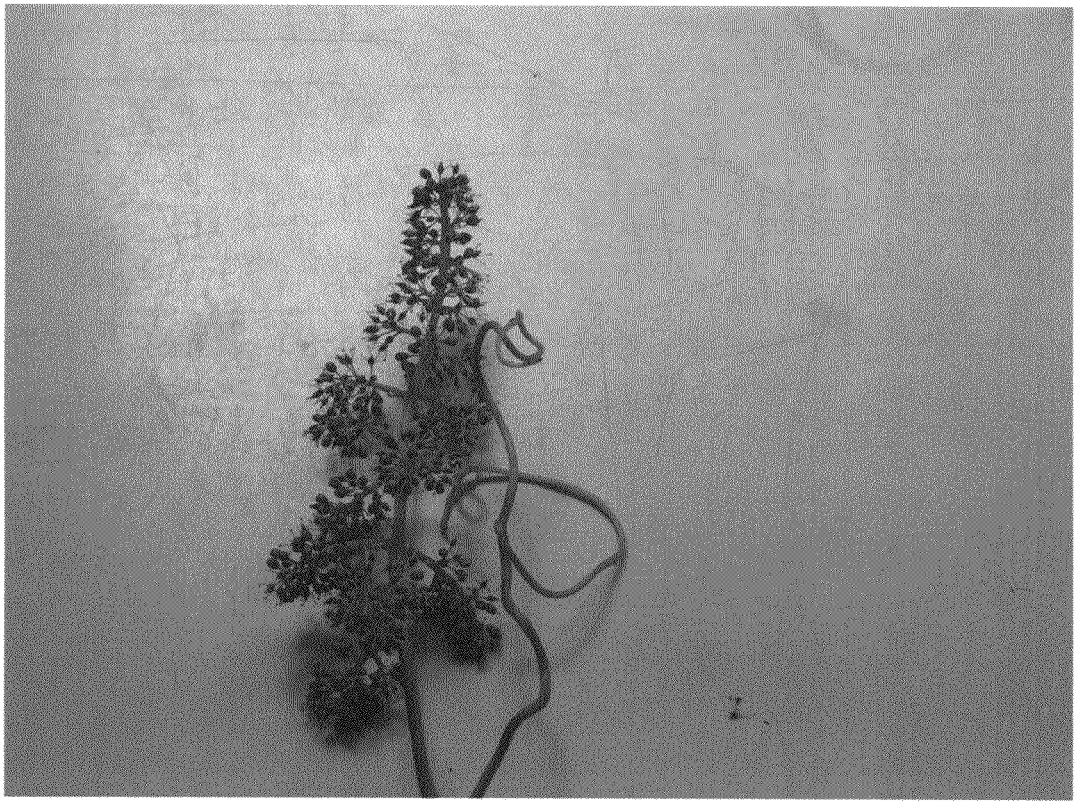
FIG. 3 shows a typical inflorescence of 'SWEET JASPER'.
Figure 4:
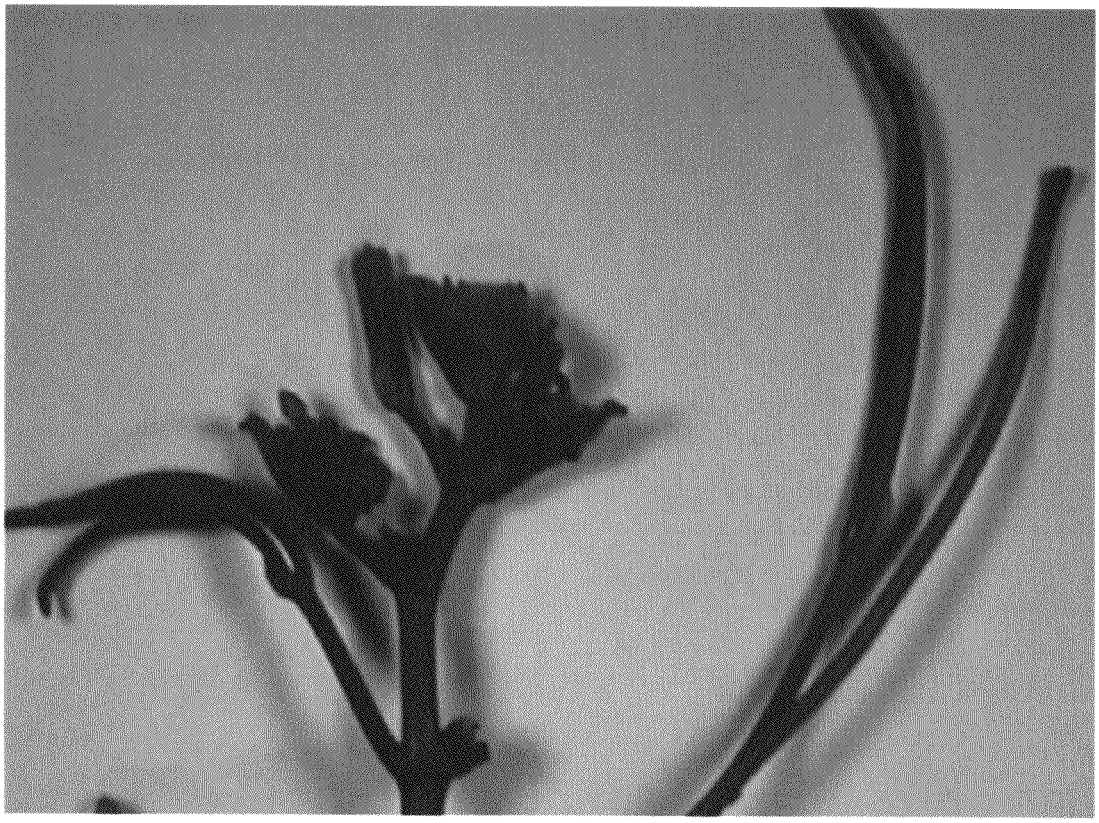
FIG. 4 shows a typical growth tip of 'SWEET JASPER'.
Figure 5:
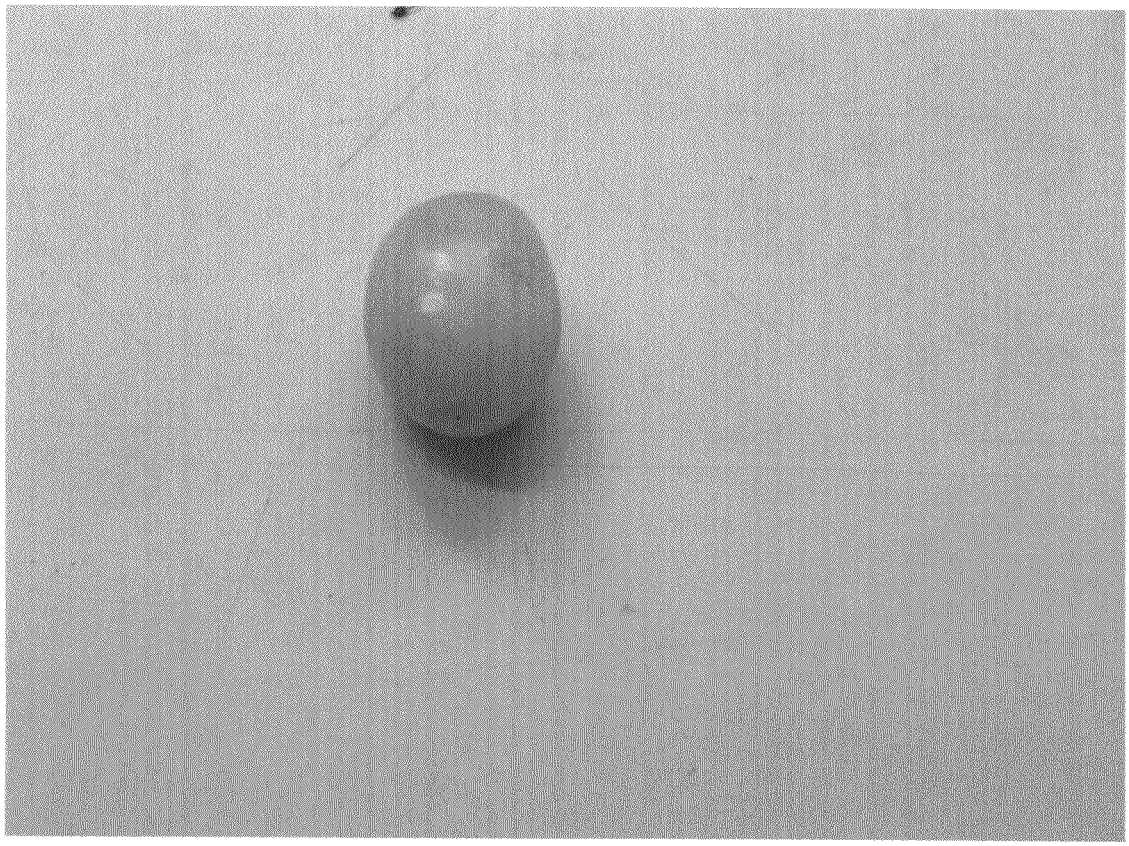
FIG. 5 shows a typical berry of 'SWEET JASPER'.

The new *Vitis vinifera* L. 'SWEET JASPER' has not been observed under all possible environmental conditions. The phenotypical descriptions and color designations stated for the new variety may vary, depending on variations in environmental factors, including weather (temperature, humidity and light intensity), day length, soil type, location and cultural conditions, without any change in the genotype of the grapevine. The following description of 'SWEET JASPER' unless otherwise noted, is based on observations and measurements taken during 2010 and 2011 at The Volcani Center, on plants grown in the vineyard located in Bet Dagan, Israel under conditions which closely approximate those generally used in commercial practice. The described plants were grafted on 'Richter110' (unpatented) and planted at a distance of 1.5 m in sandy red loam soil at an elevation of about 30 meter above sea level with drip-irrigation up to 40 $m^3$ per hectare in the peak season in the summer and Shefer 737+micro-elements 1.5 ltr. fertilizers in each 5 $m^3$ of water. Average annual rainfall is about 550 mm, with an average of 350 mm rainfall in winter (December through February). Mean diurnal minimum temperature in January is 7.2° C., and mean diurnal maximum temperature in July is 30.8° C.

Unless otherwise stated, the detailed morphological description includes observations, measurements and values based on three-year-old 'SWEET JASPER' plants grown in the vineyard at The Volcani Center, located in Bet Dagan, Israel from 2010 to 2011. Quantified measurements are expressed as an average of measurements taken from a number of plants of 'SWEET JASPER'. The measurements of any individual plant, or any group of plants, of the new variety may vary from the stated average.

Color references are made to The Royal Horticultural Society Colour Chart (R.H.S.), 1986 edition, except where general colors of ordinary significance are used. Color values were taken under daylight conditions in full sunlight in Bet Dagan, Israel.

All of the plants of 'SWEET JASPER', insofar as they have been observed, have been consistent in all the characteristics described below.

Classification:

*Botanical.*—*Vitis vinifera* L.

Parentage:

*Female or seed parent.*—*Vitis vinifera* L. 'ARO 2117' (unpatented).

*Male or pollen parent.*—*Vitis vinifera* L. 'ARO 1717' (unpatented).

Propagation: Grafting onto 'Richter110' (unpatented), Interspecific Cross, *V. berlandieri* Planch×*V. rupestris* Scheele.

Growing conditions:

*Light intensities.*—Full sunlight.

*Temperature.*—Bet Dagan — 30 meters above sea level.

| | January | February | March | April | May | June | July |
|---|---|---|---|---|---|---|---|
| Mean maximum air temperature (° C.) | 17.8 | 18.1 | 20.1 | 24.5 | 27 | 29.2 | 30.8 |
| Mean minimum air temperature (° C.) | 7.2 | 7.1 | 8.8 | 11.5 | 14.6 | 17.9 | 20.6 |
| Mean rainfall (mm) | 140.5 | 96.9 | 66.1 | 17.5 | 2.2 | — | — |

| | August | September | October | November | December |
|---|---|---|---|---|---|
| Mean maximum air temperature (° C.) | 31.2 | 30.4 | 28.3 | 24.1 | 19.7 |
| Mean minimum air temperature (° C.) | 21.2 | 19.4 | 16 | 11.8 | 8.6 |
| Mean rainfall (mm) | — | 0.4 | 20.4 | 76.2 | 130.3 |

*Fertilization.*—A balanced fertilizer with level of Shefer 737+microelements 1.5 ltr. in each 5 $m^3$ of water.

*Growth regulators.*—None applied.

*Pruning.*—As in commercial practice.

*Training.*—Y trailing cordon.

Table of characteristics:

*Plant*.—Time of vegetative bud burst: beginning of March.

*Young shoot*.—Openness of tip: closed. Density of prostrate hairs on tip: dense. Anthocyanin coloration of prostrate hairs on tip: very weak. Green color: green RHS 144 A. Green color of upper side of undeveloped leaf blade: medium green RHS 144 A with over color medium red brown RHS 166 C. Green color of lower side of undeveloped leaf blade: medium green RHS 144 B with over color medium red brown RHS 166 C. Anthocyanin coloration: medium.

*Young leaf*.—Density of hairs between main veins on lower side of blade: dense. Glossiness of upper side: medium to strong. Glossiness of lower side: weak.

*Shoot*.—Length of internode: 9-14 cm. Thickness of internode: 6-10 mm. Color of dorsal side of internode: green RHS 144 A. Anthocyanin coloration of dorsal side of internode: medium, brown red RHS 174 A. Distribution of anthocyanin coloration of dorsal side of internode: blushed. Color of ventral side of internode: green RHS 144 A. Anthocyanin coloration of ventral side of internode: weak, brown red RHS 174 A. Distribution of anthocyanin coloration of ventral side of internode: blushed. Erect hairs on internodes: absent. Height of node: about 2 cm. Swelling at node: 1-2 mm. Diameter of node: about 1.5 cm. Color of dorsal side of node: green RHS 144 A. Anthocyanin coloration of dorsal side of node: medium, brown red RHS 174 A. Distribution of anthocyanin coloration of dorsal side of node: blushed. Color of ventral side of node: green RHS 144 A. Anthocyanin coloration of ventral side of node: medium, brown red RHS 174 A. Distribution of anthocyanin coloration of ventral side of node: blushed. Pubescence of node: absent. Length of tendril: 20-40 cm. Diameter of tendril at base: 2-4 mm. Diameter of tendril at tip: about 2 mm. Pubescence of tendril: absent. Number of bifurcations per tendril: about 4. Color of tendril: light yellow green RHS 144 C. Anthocyanin coloration of tendril: medium to strong at lower part brown red RHS 174 A. Number of consecutive tendrils: not continuous.

*Inflorescence*.—Length: 13-17 cm. Maximum diameter: 5-6 cm. No. of side branches: 10-13. Attitude of side branches: horizontal. Length of longest side branch: 2-3 cm. Thickness of main axis: about 3 mm. Green color of main axis: light green RHS 144 B. Anthocyanin coloration of main axis: weak. Pubescence of main axis: weak.

*Flower*.—Sexual organs: fully developed stamen and fully developed gynoecium.

*Pedicel*.—Length: 2-3 mm. Thickness: less than 1 mm. Green color: light green RHS 144 B. Pubescence: weak.

*Stamen*.—Number: five. Length of filament: 2-3 mm. Thickness of filament: minuscule. Pubescence of filament: absent. Surface: smooth. Color: yellow RHS 150 C.

*Anther*.—Shape: transverse elliptic. Length: minuscule. Color: light green RHS 145 C.

*Pollen*.—Color: yellow RHS 150 C.

*Ovary*.—Shape: elliptic. Color: green RHS 144 A. Length: 2-3 mm. Diameter: about 1 mm. Surface: smooth.

*Style*.—Length: minuscule.

*Stigma*.—Size: minuscule. Color: yellow RHS 150 C.

*Mature leaf*.—Blade length: 15-19 cm. Blade width: 16-19 cm. Shape of blade: pentagonal. Green color of upper side: dark green RHS 147 A. Green color of lower side: dark green RHS between 146 A and 146 B. Glossiness of upper side: medium. Glossiness of lower side: weak. Profile in cross section: undulated. Blistering of upper side: weak. Number of lobes: five. Central lobe length: 6-7 cm. Central lobe width: 7-9 cm. Upper, side lobe length: 6-7 cm. Upper, side lobe width: about 7 cm. Pubescence of veins on upper side: medium. Pubescence of veins on lower side: strong. Green color of veins on upper side: green RHS 145 C. Green color of veins on lower side: yellow green between RHS 145 B and 145 C. Anthocyanin coloration of veins on upper side: absent. Anthocyanin coloration of veins on lower side: absent. Depth of upper lateral sinus: deep. Arrangement of lobes of upper leaf sinus: free. Arrangement of lobes of petiole sinus: open. Petiole sinus limited by veins: absent. Length of distal tooth: 10-13 mm. Width of distal tooth: 9-14 mm. Ratio length/width of distal tooth: medium. Shape of tooth: straight on both sides. Anthocyanin coloration of main veins on upper side of blade: absent. Density of hairs between veins on upper side of blade: medium. Density of hairs between veins on lower side of blade: medium. Length of petiole compared to main vein: shorter. Length of petiole: 8-10 cm. Petiole thickness: 4-6 mm.

*Petiole*.—Green color of upper side: green yellow RHS 145 B. Anthocyanin coloration of upper side: red RHS 59 C. Green color of lower side: green yellow RHS 145 B. Anthocyanin coloration of lower side: red RHS 59 C. Pubescence: medium.

*Fruit*.—Time of beginning of berry ripening: medium.

*Bunch*.—Length (peduncle included): about 25 cm. Maximum diameter: 12-15 cm. Weight: about 500 gr. General shape: broad triangular. Peduncle length: 3-7 cm. Peduncle thickness: about 5 mm. Peduncle color: light green RHS 144 C with anthocyanin coloration pink RHS 181 B. Peduncle lignification: absent. Density: dense.

*Pedicel*.—Length: 8-11 mm. Thickness: 2-3 mm. Color: green RHS 145 A.

*Berry*.—Detachment: medium. Length: 26-34 mm. Diameter: 18-22 mm. Weight: about 7.6 gr. Shape in profile: cylindrical. Shape in cross section: rounded. Depression at distal end: absent. Color of skin (without bloom): yellowish green between RHS 145 B and 145 C. Amount of bloom: none Surface: Smooth, slightly ridged. Thickness of skin: thin. Adherence of skin to flesh: strong. Flesh color: very light green RHS 145 C. Flesh anthocyanin coloration: absent. Firmness of flesh: firm. Juiciness of flesh: low. Particular flavor: absent. Formation of seeds: absent.

*Woody shoot*.—Length of node: variable. Main color (without bloom): brown RHS 177 B. Relief of surface: rough. Shape in cross section: ribbed. Diameter: about 10 mm. Lenticels: not visible.

Usage: Table grape.

Disease\pest resistance: No atypical resistance has been noted.

What is claimed is:

1. A new and distinct grapevine variety, referred to as 'SWEET JASPER', as herein described and illustrated by the characteristics set forth above.

* * * * *